United States Patent [19]

Dick

[11] Patent Number: 5,393,767

[45] Date of Patent: Feb. 28, 1995

[54] INSECT CONTROL WITH SUBSTITUTED TRIAZOLE AND TETRAZOLE COMPOUNDS

[75] Inventor: Michael R. Dick, Carmel, Ind.

[73] Assignee: DowElanco, Indianapolis, Ind.

[21] Appl. No.: 112,498

[22] Filed: Aug. 26, 1993

[51] Int. Cl.$^6$ .................. A01N 43/40; A01N 43/42; A01N 43/64; A01N 43/90

[52] U.S. Cl. ..................... 514/381; 514/299; 514/304; 514/305; 514/326; 514/340; 514/383; 514/384

[58] Field of Search ............ 514/381, 299, 304, 305, 514/326, 340, 383, 384

[56] References Cited

U.S. PATENT DOCUMENTS

| | | | |
|---|---|---|---|
| 5,134,146 | 7/1992 | Showell et al. | 514/299 |
| 5,200,419 | 4/1993 | Hobbs et al. | 514/323 |

FOREIGN PATENT DOCUMENTS

| | | |
|---|---|---|
| 0239309 | 9/1987 | European Pat. Off. |
| 0427390A2 | 5/1991 | European Pat. Off. |

OTHER PUBLICATIONS

Saunders et al, J. Chem. Soc. Chem. Commun. 1618–1619 (1988).

Street et. al.; J. Med. Chem., 33, 2690–2697 (1990).

H. J. Wadsworth et al. "Synthesis and Muscarinic Activities of Quinuclidin-3-yltriazole and -tetrazole Derivatives", J. Med. Chem. 1992, 35, 1280–1290.

S. M. Jenkins et al, "Substituent Variation in Azabicyclic Triazole-and Tetrazole-Based Muscarinic Receptor Ligands", J. Med. Chem. 1992, 35, 2392–2406.

*Primary Examiner*—Allen J. Robinson
*Attorney, Agent, or Firm*—Donald R. Stuart

[57] ABSTRACT

Insects, especially sucking insects, such as brown planthoppers, and phytophageous mites, such as two-spotted spider mites, are controlled by applying an triazole or tetrazole compound substituted on a carbon atom by an aliphatic nitrogen heterocyclic moiety composed of at least one five or six membered ring. The compound exo-3-(5-aminotetrazol-2-yl)-1-azabicyclo[2.2.1]heptane is typical.

11 Claims, No Drawings

INSECT CONTROL WITH SUBSTITUTED TRIAZOLE AND TETRAZOLE COMPOUNDS

The present invention relates to a method of controlling insects and arachnids by treatment with insecticidal heterocyclic compounds and to insecticidal compositions useful in the method.

The control of insects and arachnids is critical to modern agriculture and to the maintenance of public health. Although many organic compounds are known to be toxic to insects and methods of killing and controlling insects based on them are known, different organic compounds that are more efficacious, are less toxic to mammals, are more compatible with the environment, are not cross-resistant with established insecticides, are less expensive, or have other new or improved properties are constantly sought and when found are highly valued.

U.S. Pat. No. 5,200,419 discloses certain nonaromatic 1-azabicyclic ring systems substituted with tetrazolyl moieties as pharmaceutical agents; and European Patent Application 427,390 A2 discloses certain nonaromatic 1-azabicyclic ring systems substituted with pyrazolyl, triazolyl, or tetrazolyl moieties as pharmaceutical agents.

Jenkins et al., *J. Med. Chem.* 1992, 35, 2392–2406, and Wadsworth et al., *J. Med. Chem.* 1992, 35, 1280–1290 describe preparation of azabicylic triazole and tetrazole compounds utilized in this invention. Both articles are concerned with preparation of candidate drugs for Alzheimer's disease, and neither suggests that the compounds have insecticidal activity.

It has now been found that certain substituted triazole and tetrazole derivatives are toxic to insects and arachnids and can be used as the active agent in a method of controlling insects and arachnids. More specifically, a method of killing or controlling insects and arachnids has been found which method comprises contacting said insects and arachnids or the locus thereof with an insecticidal or arachnicidal amount of a compound of Formula I or Formula II:

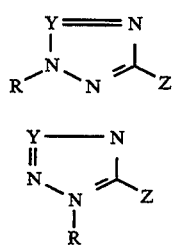

wherein
Y represents CH or N;
Z represents H, F, Cl, Br, CN, $CO_2R^1$, $CONH_2$, $CONHR^1$, $CONR_1R^1$, $OR^1$, $SR^1$, $NH_2$, $NHR^1$, $NR^1R^1$, $NHOR^1$, cyclopropyl, $CH=CH_2$, $C\equiv CR^2$, or $C_1$-$C_2$ alkyl optionally monosubstituted with F, OH, $OR^1$, $SR^1$, $NH_2$, $NHR^1$, $NR^1R^1$, $CO_2R^1$, $CONH_2$, $CONHR^1$, or $CONR_1R^1$;
$R^1$ is $C_1$-$C_2$ alkyl, $CH_2-C\equiv CH$, $CH_2-CH=CH_2$, benzyl, or cyclopropylmethyl;
$R^2$ is H or $SIR^3$;
$R^3$ is $C_1$-$C_4$ alkyl;

R is an aliphatic nitrogen containing heterocyclic moiety selected from groups $R_a$ through $R_k$ where $R_a$ through $R_k$ are as follows:

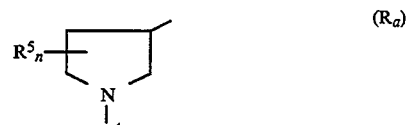

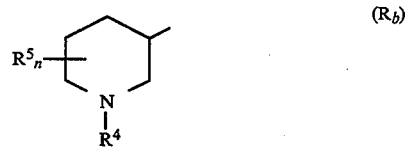

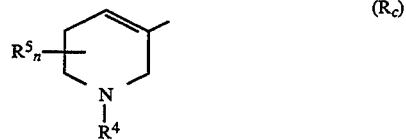

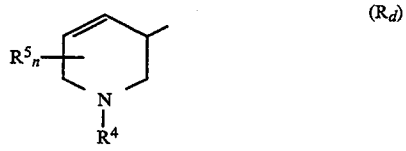

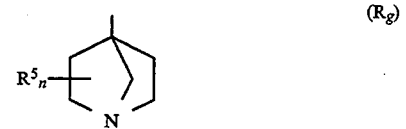

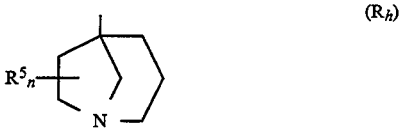

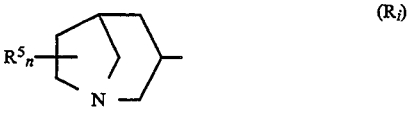

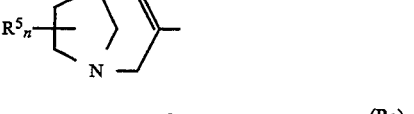

wherein $R^4$ represents H or $C_1$–$C_2$ alkyl;

$R^5$ represents F, Cl, Br, OH, $CO_2R^1$, $C_1$–$C_4$ alkyl, or $C_1$–$C_4$ alkoxy;

n represents the integer 0, 1, or 2;

or an agriculturally acceptable acid addition salt thereof; or otherwise causing an insecticidal or arachnicidal amount of said compound to be present within said insects or arachnids.

Certain compounds are preferred, viz.:

Compounds of Formulas I and II wherein R is a group $R_f$, i.e. compounds wherein R is 1-azabicyclo[2.2.1]heptan-3-yl (azanorbornyl);

Compounds of Formula I, particularly compounds of Formula I wherein Y is N, i.e. tetrazole derivatives;

Compounds of Formula I wherein Y is N and Z is $NH_2$, i.e. 5-aminotetrazole derivatives.

Particularly preferred is exo-3-(5-aminotetrazol-2-yl)-1-azabicyclo[2.2.1]heptane.

It has further been found that compositions containing at least one agriculturally acceptable adjuvant or carrier in combination with an insecticidal or arachnicidal amount of a compound of Formulas I and II can be employed for the kill and control of insects and arachnids.

DETAILED DESCRIPTION OF THE INVENTION

The substituent R of Formulas I and II is an aliphatic nitrogen heterocycle moiety selected from those depicted above, which includes pyrrolidines, piperidines, 1,2,5,6-tetrahydropyridines, 1-azabicyclo[3,2,1]octanes, 1-azabicyclo[3,2,1]oct-3-enes, quinuclidines (1-azabicyclo-[2,2,2]octanes), azanorbornanes (1-azabicyclo[2,2,1-]heptanes), and the like. Such heterocycles generally involve at least one 5 or 6 membered ring having one nitrogen atom. It is generally preferred that the triazolyl or tetrazolyl group be bonded to the aliphatic nitrogen heterocyclic substituent at a carbon atom beta to the nitrogen atom. The aliphatic nitrogen heterocyclic substituent may, itself be substituted, as noted above ($R^4$ and $R^5$). The substituents designated as $R^5$ may be attached to any carbon atom of the heterocycle. Heterocyclic moieties not possessing any such substituents on a carbon atom (n represents the integer 0), however, are often preferred. Compounds wherein the substituent $R^4$ represents hydrogen or methyl are often preferred. The especially preferred aliphatic nitrogen heterocyclic substituents include 1,2,5,6-tetrahydropyridin-3-yl, 1-methyl-1,2,5,6-tetrahydropyridin-3-yl, 1-azabicyclo [2,2,1]heptan-3-yl and 1-azabicyclo[2,2,2]octan-3-yl.

The substituent Z of Formulas I and II may be any of the atoms or groups mentioned hereinabove. The preferred substituents include amino and methyl groups.

The compounds utilized in the present invention can be employed as their acid addition salts; such salts form reversibly depending on the pH of the medium in which they are placed. Acid addition salts form because the compounds all contain an amino nitrogen atom in the aliphatic R group, which atom makes the molecule basic and capable of forming such salts. The agriculturally acceptable acid addition salts of the present invention are those derived from acids that are not significantly deleterious to any crop being treated, to the applicator, to the environment, or to the ultimate user of any crop being treated and that does not interfere with the insecticidal action of the compound of Formulas I and II. Suitable acids include mineral acids, such as hydrochloric acid, sulfuric acid, phosphoric acid, and the like. They also include carboxylic acids, such as acetic acid, butyric acid, dodecanoic acid, tartaric acid, citric acid, glycolic acid, lactic acid, maleic acid, benzoic acid, and the like, and sulfonic acids, such as methanesulfonic acid, benzenesulfonic acid, and the like. The acid addition salts are readily prepared by procedures well-known to those in the art, such as by simply adding a stoichiometric amount or an excess of an appropriate acid to a compound of Formula I, or II in a solvent. The method of the present invention is predicated on causing an insecticidal or arachnicidal amount of a compound of Formula I or II to be present within insects or arachnids and, thereby, killing or controlling the insects or arachnids. It is possible and is within the scope of the invention to cause a compound of Formula I, or Formula II wherein Z represents amino ($NH_2$) to be present within insects or arachnids by contacting the insects or arachnids with a derivative of that compound, which derivative is converted within the insects or arachnids to a compound Formula I or II wherein Z represents amino. Such compounds, which can be referred to as pro-insecticides, include compounds containing a Z substituent that can be converted to $NH_2$ by chemical processes, such as hydrolysis, oxidation, reduction, and the like, that are either enzymatic or non-enzymatic in nature. Suitable substituents include N-acylamino, N-substituted imino, and N-sulfenyl amino groups, and the like. Some examples, wherein hydrocarbyl refers to an aliphatic or aromatic hydrocarbon moiety optionally substituted with halogen, hydroxy, alkoxy, cyano, or nitro, or the like, are illustrated below:

NH—CO(hydrocarbyl)
NH—$CO_2$(hydrocarbyl)
NH—CO—NH(hydrocarbyl)
NH—$COCO_2$(hydrocarbyl)
NH—C(S-(hydrocarbyl))=N(hydrocarbyl)
NH—CH(O-(hydrocarbyl))(hydrocarbyl)
NH—S(hydrocarbyl)
NH—S-N(hydrocarbyl)$_2$
N=CH(hydrocarbyl)
NH—CH(OH)(hydrocarbyl)

Compounds containing such substituents can be prepared from compounds of Formula I or II wherein Z represents $NH_2$ by well-established methods known to those in the art. For example, N-acyl derivatives can be prepared by treatment with an acyl halide or anhydride, N-substituted imino derivatives can be prepared by treatment with aldehydes, urea derivatives can be prepared by treatment with isocyanates, N-sulfenyl derivatives can be prepared by treatment with a sulfenyl chloride, carbamate derivatives can be prepared by treatment with a chloroformate ester, and isothiourea derivatives can be prepared by treatment with first an isothiocyanate and then a hydrocarbyl halide.

It is further possible and within the scope of the invention to cause a compound of Formula I or Formula II wherein $R^4$ represents hydrogen (H) to be present within insects and arachnids by contacting the insects or arachnids with a derivative of that compound, which derivative is converted within the insects or arachnids to a compound of Formula I or II wherein $R^4$ represents hydrogen. Such compounds are also pro-insecticides. Suitable compounds include those wherein the N-H hydrogen atom of such compounds is replaced by a substituent that can be removed by hydrolysis, oxidation, or reduction in either enzymatic or non-enzymatic reactions. Typical substituents include alkoxymethyl and alkylthiomethyl groups, alkanoyloxymethyl groups, sulfenyl groups, and sulfeneamino groups. Some examples, wherein hydrocarbyl refers to an aliphatic or aromatic hydrocarbon moiety optionally substituted with halogen, hydroxy, alkoxy, cyano, or nitro, or the like are illustrated below:

$CH_2$—O(hydrocarbyl)
S(hydrocarbyl)
N—$CH_2$—S(hydrocarbyl)
S—N hydrocarbyl$_2$
$CH_2$—OCO(hydrocarbyl)
S—N(hydrocarbyl)
$CO_2$(hydrocarbyl)

Compounds of these types can be prepared from compounds of Formulas I or II wherein $R^4$ represents H by methods well-established in the art. For example, alkyloxymethyl, alkylthiomethyl, and alkanoyloxymethyl substituted compounds can be prepared by alkylation with the corresponding chloromethyl alkyl ether, thioether, or ester. The sulfenyl type substituted compounds can be prepared by reaction with the corresponding sulfenyl halide.

The compounds of Formulas I or II in most cases possess centers of asymmetry in the R moiety and, therefore, may exist as optical and/or geometric isomers. The formulas and descriptions given herein relate to all such isomers. In the case of the bicyclic R moieties, the geometric isomers are usually referred to as exo or endo isomers. While one optical or geometric isomer may possess better insecticidal properties than another, all compounds of Formulas I or II have some insecticidal properties.

The compounds employed in the method of the present invention are generally known and many specific examples of their preparation have been described in the art. For example, U.S. Pat. No. 5,200,419; European Patent Application 427,390; Jenkins et al., *J. Med. Chem.* 1992, 35, 2392–2406, and Wadsworth et al., *J. Med. Chem.* 1992, 35, 1280–1290 describe preparation of azabicyclic triazole and tetrazole compounds utilized in this invention.

A preferred method for preparing many of the compounds of Formula (I) is illustrated in the following scheme:

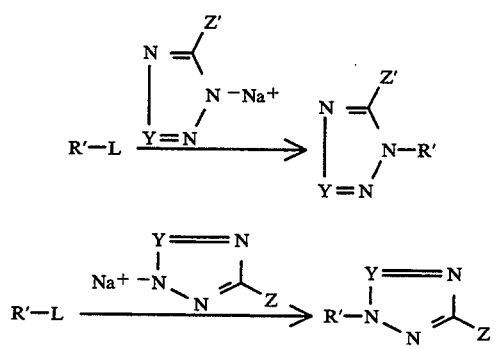

where
L is leaving group, such as Br or methanesulfonyloxy; and
R' is a group selected from $R_a$, $R_b$, $R_c$, $R_d$, $R_e$, $R_f$, $R_i$, $R_j$ and $R_k$.

The method can also be used to prepare compounds of Formula (II).

Jenkins et al., *J. Med. Chem.* 1992, 35, 2392–2406, describes a number of routes for preparing compounds of Formula (I) wherein Y is CH, including those illustrated in the following schemes:

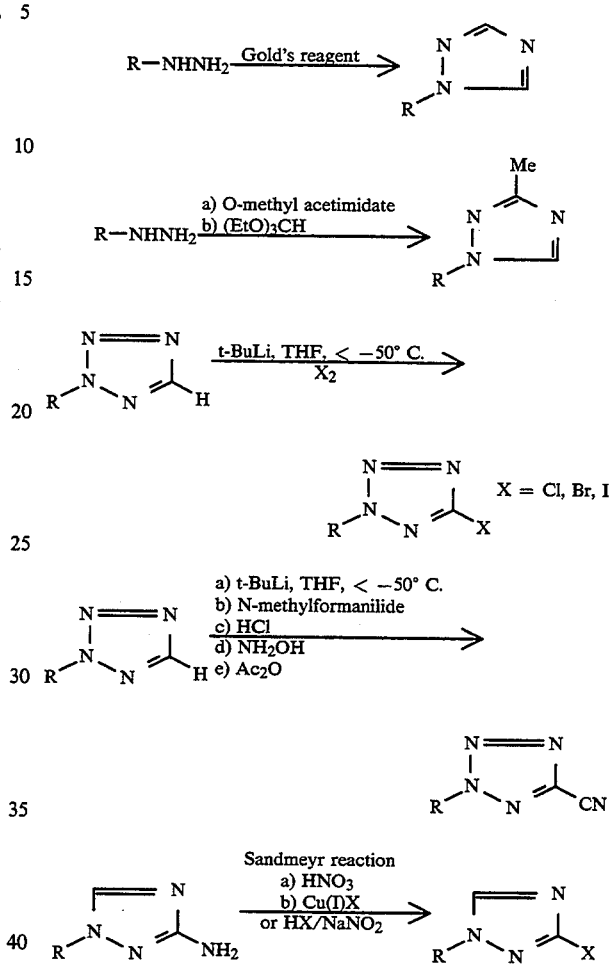

Preparation of Key Intermediates endo-3-Hydroxy-1-azabicyclo[2.2.1]heptane (7), and the corresponding mesylate (8), can be prepared by the procedure described by Jenkins et al., *J. Med. Chem.* 1992, 35, 2392–2406, as illustrated in scheme 1:

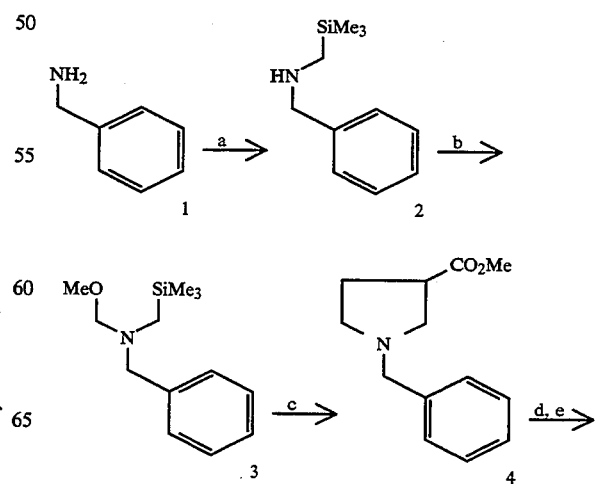

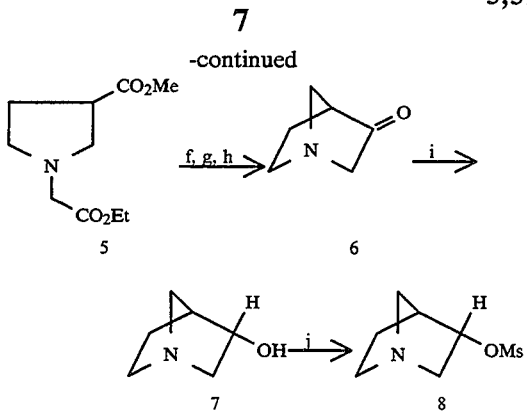

a) ClCH₂SiCH₃, Δ. b) nBuLi, THF, −70° C; MeOCH₂Cl. c) CH₂=CHCO₂Me, TFA, CH₂Cl₂, 0° C. to rt. d) EtO₂CCH₂Br, K₂CO₃, EtOH, reflux. e) H₂, Pd/C, EtOH/HOAc. f) KOtBu, toluene, reflux. g) 12M HCl, reflux. h) K₂CO₃. i) H₂, PtO₂, EtOH. j) MsCl, Et₃N, CH₂Cl₂, 0° C. to rt.

3-[(Methanesulfonyl)oxy]-1-azabicyclo[2.2.2]octane can be prepared from commercially available quinuclidi-3-ol by the procedure illustrated in scheme 2:

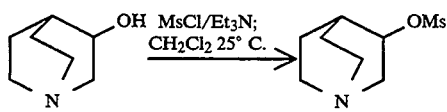

The starting material for pyrrolidine analogs can be prepared by the procedure illustrated in scheme 3:

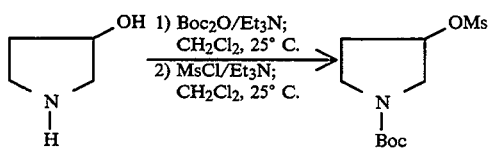

EXPERIMENTAL

Preparation 1

(±) 3-Methanesulphonyloxy-1-azabiyclo[2.2.2]octane

Quinuclidin-3-ol (5.00 g; 39.3 mmol), methanesulphonyl chloride (3.8 mL; 49 mmol; 1.2 eq), and triethylamine (8.5 mL; 60.0 mmol) were combined in 100 mL of dichloromethane at 0° C. The ice bath was removed and the mixture was stirred for 1.5 hr. The reaction was then quenched with saturated NaHCO₃, and extracted with dichloromethane (2×). The combined organics were dried (Na₂SO₄), filtered, and evaporated. Yield 7.3 g. (36 mmol, 90%).

¹H NMR (CDCl₁₃) δ4.82 (m, 1H, H-3), 3.38 (ddd, 1H), 3.03 (s, 3H, SO₂CH₃), 2.81–2.89 (m, 5H), 2.14 (m, 1H, H-4), 1.67–1.78 (m, 3H), and 1.41–1.45 (m, 1H).

Preparation 2 endo-3-Methanesulfonyloxy-1-azabicyclo[2.2.1]heptane

The title compound was prepared from endo-1-azabicyclo[2.2.1]heptan-3-ol using the same procedure as in Preparation 1. The mesylate was isolated as a yellow solid in 95% yield.

¹H NMR (CDCl₁₃) δ5.04 (dddd; J=1.5, 3.2, 4.6, and 9.0 Hz; H-3), 3.12 (ddd; J=2.4, 9.0, and 13.5 Hz; H-2exo), 2.98 (s, 3H, SO₂CH₃), 2.88 (m, 2H, H-2endo+H-7a), 2.62 (m, 2H, H-4+H-6exo), 2.44 (ddd; J=0.9, 4.1, and 10.2 Hz; H-7b), 2.35 (ddd; J=3.6, 4.1, and 13.5 Hz; H-6endo), 1.85–1.92 (m, 1H, H-5a), and 1.48–1.56 (m, 1H, H-5b). ¹³C NMR (CDCl₃) δ81.8 (C-3), 61.0 (C-2), 59.1 (C-7), 54.0 (C-6), 42.1 (C-4), 38.1 (SO₂CH₃), and 21.2 (C-5).

Example 1

(+) 3-(1,2,4-triazol-1-yl)-1-azabicyclo[2.2.2]octane (Compound 1)

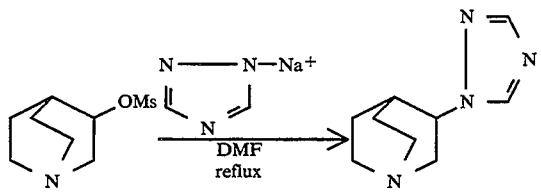

To a solution of (±)3-methanesulphonyloxy-1-azabiyclo[2.2.2]octane (1.3 g; 6.3 mmol) in dry DMF (20 mL) was added 1,2,4-triazole, sodium salt (1.5 g; 21 mmol). The resulting mixture was refluxed for 2 hours. The reaction mixture was cooled to room temperature and concentrated to dryness. The residue was taken up into 1M Na₂CO₃ and extracted into CH₂Cl₂ (3×50 mL). The organics were combined, dried (Na₂SO₄), filtered, and evaporated to yield 0.57 g of a crude yellow oil. MPLC (Al₂O₃; 2% MeOH/CH₂Cl₂) provided two fractions, the first containing a byproduct and the second containing the triazole. Yield 300 mg (27%).

¹H NMR (CDCl₁₃) δ8.10 (s, 1H, H-3′), 7.89 (s, 1H, H-5′), 4.43 (m, 1H, H-3), 3.34–3.47 (m, 2H), 3.07 (m, 1H), 2.81–2.89 (m, 3H), 2.14 (m, 1H, H-4), 1.67–1.78 (m, 3H, 2H-8+H-5a), and 1.41–1.45 (m, 1H, H-5b). ¹³C NMR (CDCl₁₃) δ151.5 (d, C-3′), 140.7 (d, C5′), 56.7 (d, C-3), 52.0 (t, C-2), 46.8 (t, C-7), 46.3 (t, C-6), 27.8 (d, C-4), 25.6 (t, C-8), and 19.8 (t, C-5).

Example 2

(+) 3-(5-Aminotetrazol-2-yl)-1-azabicyclo[2.2.2]octane (Compound 2)

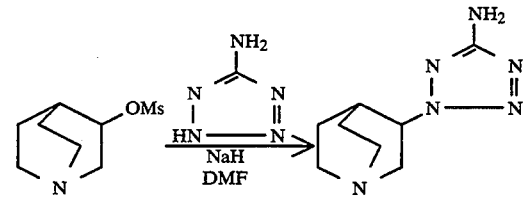

To a solution of 5-aminotetrazole monohydrate (4.8 g; 143.7 mmol) in dry DMF (80 mL) was added sodium hydride (5.76 g; 60 % oil dispersion; 144 mmol). The resulting mixture was heated to 60° C. for 1 hour, then cooled to room temperature. This solution was added to one containing (±)3-methanesulphonyloxy-1-azabiyclo[2.2.2]octane (6.0 g; 29.5 mmol) in DMF (20 mL). The resulting mixture was refluxed for two hours, then cooled to room temperature and concentrated under vacuo. The residue was washed with hexanes, taken up into 1M Na₂CO₃, and extracted into CH₂Cl₂ (3×75 mL). The organics were combined, dried (Na₂SO₄), filtered, and evaporated. Crude yield 1.4 g. Flash chromatography (Al₂O₃; 3% MeOH/CH₂Cl₂)provided two fractions, the first containing a by-product, and the second the desired product. Yield 300 mg. (5%).

¹H NMR (CDCl₁₃) δ4.68 (m, 1H, H-3), 4.44 (bs, 2H, NH₂), 3.68 (ddd; J=1.9, 5.0, and 14.4 Hz; H-2a), 3.36 (m, 1H, H-2b), 3.06 (m, 1H, H-6a), 2.80-2.94 (m, 3H, 2H-7+H-6b), 2.31 (m, 1H, H-4), 1.70-1.80 (m, 2H, 2H-8), 1.60-1.70 (m, 1H, H-5a), and 1.35-1.45 (m, 1H, H-5b). ¹³C NMR (CDCl₁₃) δ165.8 (s, C-5'), 60.9 (d, C-3), 50.7 (t, C-2), 46.3 (t, C-7), 45.9 (t, C-6), 27.0 (d, C-4), 24.8 (t, C-8), and 19.5 (t, C-5). m/e 194 (M+).

Example 3

(±) exo-3-(5-Aminotetrazol-2-yl)-1-azabicyclo[2.2.1-]heptane (Compound 3)

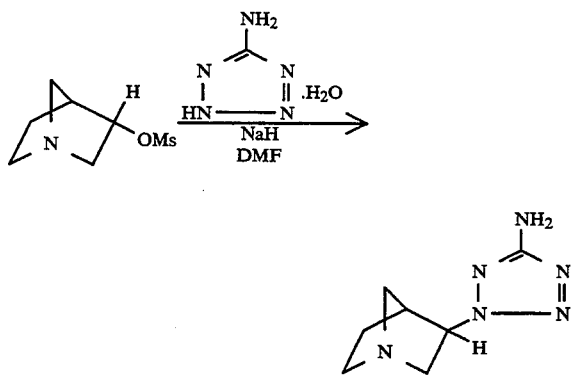

To a solution of 5-aminotetrazole monohydrate (2.0 g; 19.4 mmol) in dry DMF (20 mL) was added sodium hydride (0.800 g of a 60% oil dispersion; 20 mmol). Following evolution of hydrogen, powdered mol sieves (1 g) and endo-3-methanesulfonyloxy-1-azabicyclo [2.2.1]heptane (1.0 g; 5.2 mmol) were added, and the resulting mixture was brought to reflux for 2 hours. The mixture was cooled to room temperature and the solvent removed under reduced pressure. The residue was taken up into 1M Na₂CO₃ (aq) and extracted with CH₂Cl₂ (3×). The combined organics were dried (Na₂SO₄), filtered and evaporated. The crude residue (700 mg) was purified by flash chromatography (Al₂O₃; 2% MeOH/CH₂Cl₂) to provide exo-3-(5-aminotetrazol-2-yl)-1-azabicyclo[2.2.1]heptane as a white solid. Yield 230 mg (25%). MP 127°-130° C.

¹H NMR (CDCl₁₃) δ54.6 (bs, 2H, NH₂), 4.40 (ddd; J=1.0, 4.2, and 7.4 Hz; H-3), 3.28 (ddd; J=2.4, 4.2, and 13.1 Hz; H-2exo), 3.05 (ddd; J=2.6, 7.4, and 13.1 Hz; H-2endo), 3.02 (bd, 1H, H-7a), 2.96 (bd, 1H, H-4), 2.85 (m, 1H, H-6exo), 2.47 (m, 1H, H-6endo), 2.41 (bd, 1H, H-7b), 1.70-1.75 (m, 1H, H-5a), and 1.20-1.25 (m, 1H, H-5b). ¹³C NMR (CDCl₃) δ166.0 (C-5'), 65.6 (C-3), 61.4 (C-2), 58.1 (C-7), 53.5 (C-6), 43.3 (C-4), and 27.8 (C-5). m/e 180 (M+).

Example 4

(+) exo-3-[5-Bromotetrazol-2-yl]-1-azabicyclo[2.2.1]heptane (Compound 4)

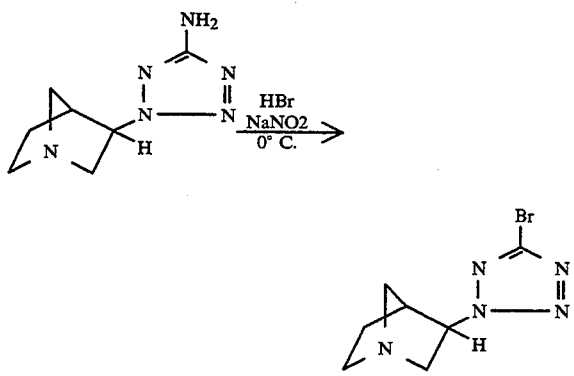

To a solution of Compound 3 (800 mg; 4.4 mmol) in conc. HBr (49%, 10 mL) at 0° C. was added a solution of sodium nitrite (680 mg; 9.85 mmol) in water (0.5 mL). The resulting solution was stirred at 0° C. for 0.5 hours. The reaction mixture was then quenched with 1M Na₂CO₃ (aq) and extracted into CH₂Cl₂ (3×). The organics were combined, dried (Na₂SO₄), filtered, and evaporated. The residual yellow oil was purified via flash chromatography (1% MeOH/CH₂Cl₂ on Al₂O₃) providing 730 mg of the title compound as a waxy, off-white solid (68% yield). MP 64°-66° C.

¹H NMR (CDCl₃) δ4.61 (ddd; J=1.0, 4.2, and 7.4 Hz; H-3), 3.28 (ddd; J=2.4, 4.3, and 13.2 Hz; H-2exo), 3.15 (ddd; J=2.6, 7.4, and 13.2 Hz; H-2endo), 3.00-3.10 (m, 2H, H-7a+H-4), 2.85 (m, 1H, H-6exo), 2.47 (m, 2H, H-6endo+H-7b), 1.75-1.80 (m, 1H, H-5a), and 1.23-1.28 (m, 1H, H-5b). ¹³C NMR (CDCl₃) δ142.4 (s, C-5'), 67.1 (d, C-3), 61.9 (t, C-2), 58.3 (t, C-7), 53.5 (t, C-6), 43.7 (d, C-4), and 27.8 (t, C-5). Analysis: theory: C, 34.44; H, 4.13; N, 28.69. found: C, 34.33; H, 4.22; N, 28.54.

Example 5

3-[5-Aminotetrazol-2-yl)-2,3,4,5-tetrahydropyrrole Hydrochloride (Compound 5)

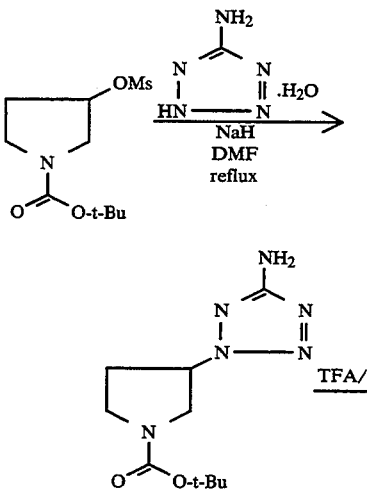

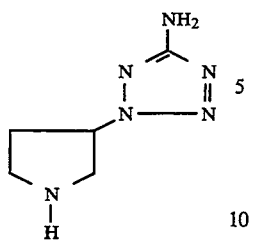

a) To a solution of 5-aminotetrazole monohydrate (1.5 g; 14.5 mmol) in dry DMF (10 mL) under $N_2$ (g) was added sodium hydride 0.58 g of a 60% oil dispersion; 14.5 mmol) followed, after 1 hour, by a solution of 1-tert-butylcarbomethoxy-3-methanesulfonyloxypyrrolidine (0.80 g; 2.9 mmol) in DMF (5 mL). The resulting mixture was refluxed for 2 hours. The solvent was removed in vacuo and the residue washed with hexanes. The resulting amorphous solid was dissolved in $NaHCO_3$ (sat) and extracted into $CH_2Cl_2$ (3×). The organics were combined, dried ($Na_2SO_4$), filtered and evaporated. The residual oil was purified (MLC; $SiO_2$; 4% $CH_2Cl_2$/MeOH) to provide the tetrazole as a clear oil. Yield 380 mg.

b) To a solution of the resulting oil (400 mg; 1.6 mmol) in $CH_2Cl_2$ (10 mL) at room temperature was added trifluoroacetic acid (2 mL). The solvent was removed under vacuo to yield 0.59 g a clear viscous oil. The residue was treated with HCl (2×2 mL) each time removing the solvent under vaccuo. The residue (340 mg) was recrystallized from methanol to provide the hydrochloride salt of the target compound. Yield 310 mg (51%).

$^1$H NMR ($D_2O$) δ5.18 (m, 1H, H-3), 3.61 (m, 1H), 3.06 (m, 1H), 2.71 (t, 2H), and 2.30–2.45 (m, 2H). Analysis: theory: C, 31.50; H, 5.82; N, 44.09. found: C, 31.96; H, 6.24; N, 43.36.

Example 6

3-[3-Amino-1,2,4-triazol-1-yl]-2,3,4,5-tetrahydropyrrole Dihydrochloride (Compound 6)

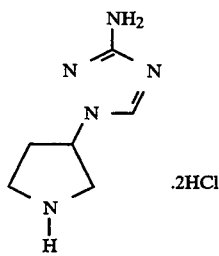

The title compound was prepared from 1-tert-butyl-carbomethoxy-3-methanesulfonyloxy-pyrrolidine using the procedure of example 5 except using 3-amino-1,2,4-trizaole. Crystallization from methanol/ether provided the title compound as a dihydochoride salt (67%).

$^1$H NMR ($D_2O$) δ7.62 (s, 1H, H-5'), 4.61 (m, 1H, H-3), 3.56 (m, 1H), 2.91 (m, 1H), 2.62 (t, 2H), and 2.16–2.30 (m, 2H). Analysis: theory: C, 31.87; H, 5.80; N, 30.97. found: C, 31.90; H, 6.12; N, 30.71.

Example 7

(±) exo-3-[5-(Methylthio)tetrazol-2-yl]-1-azabicyclo[2.2.1]heptane (Compound 7)

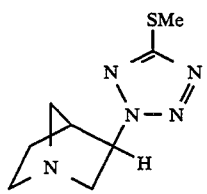

The title compound was prepared from endo-1-azabicyclo[2.2.1]-heptan-3-ol using the procedure of example 1 with 5-(methylthio)tetrazole. Flash chromatography (alumina; 1 hexanes/EtOAc) provided the title compound as a yellow oil in 31% yield.

$^1$H NMR ($CDCl_3$) δ4.54 (ddd; J=1.0, 4.2, and 7.4 Hz; H-3), 3.28 (ddd; J=2.4, 4.3, and 13.2 Hz; H-2exo), 3.10 (ddd; J=2.6, 7.4, and 13.2 Hz; H-2endo), 3.02 (bd, 1H, H-7a), 2.99 (bd, 1H, H-4), 2.85 (m, 1H, H-6exo), 2.61 (s, 3H, CH3), 2.47 (m, 1H, H-6endo), 2.42 (bd, 1H, H-7b), 1.72–1.77 (m, 1H, H-5a), and 1.26–1.30 (m, 1H, H-5b). $^{13}$C ($CDCl_3$) δ164.7 (s, c-5'), 66.3 (d, C-3), 61.8 (t, C-2), 58.3 (t, C-7), 53.6 (t, C-6), 43.6 (d, C-4), 27.9 (t, C-5), and 14.4 (q, SCH3). m/e 180 (M+).

Example 8

(±) exo-3-(tetrazol-2-yl)-1-azabicyclo[2.2.1]heptane (8)

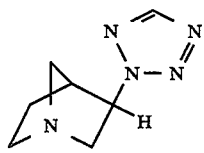

The title compound was prepared from endo-1-azabicyclo[2.2.1]heptan-3-ol with 1H-tetrazole using the procedure described in example 1. Flash chromatography ($Al_2O_3$; 2% MeOH/$CH_2Cl_2$) and subsequent bulb-to-bulb distillation (80°–90° C. 0.02 mm Hg) gave the desired tetrazole in 40% yield.

$^1$H NMR ($CDCl_3$) δ8.37 (s, 1H, H-5'), 4.58 (ddd; J=1.0, 4.2, and 7.4 Hz; H-3), 3.22 (ddd; J=2.4, 4.2, and 13.1 Hz; H-2exo), 3.07 (ddd; J=2.6, 7.4, and 13.1 Hz; H-2endo), 2.97 (bd, 1H, H-7a), 2.94 (bd, 1H, H-4), 2.79 (m, 1H, H-6exo), 2.45 (m, 1H, H-6endo), 2.37 (bd, 1H, H-7b), 1.66–1.72 (m, 1H, H-5a), and 1.22–1.27 (m, 1H, H-5b). $^{13}$C ($CDCl_3$) δ153.4 (s, C-5'), 66.3 (d, C-3), 61.7 (t, C-2), 58.1 (t, C-7), 53.3 (t, C-6), 43.5 (d, C-4), and 27.6 (t, C-5).

Example 9

(±) exo-3-(3-Amino-1,2,4-triazol-1-yl)-1-azabicyclo[2.2.1-]heptane (Compound 9)

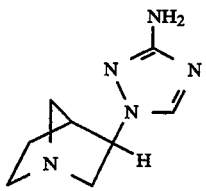

The title compound was prepared from endo-1-azabicyclo[2.2.1]heptan-3-ol with 3-amino-1,2,4-triazole using the procedure described in example 1. Flash chromatography ($Al_2O_3$; 5% $MeOH/CH_2Cl_2$) and subsequent trituration with acetone gave the title compound as a white solid. (Yield 4%). MP: 153°–155° C.

$^1$H NMR ($d_6$-DMSO/CDCl$_3$) δ7.24 (s, 1H, H-5'), 4.2 (bs, 2H, NH$_2$), 3.40 (ddd; J=1.0, 4.2, and 7.4 Hz; H-3), 2.40–2.55 (m, 3H, 2H-2+H-7a), 2.25 (m, 1H, H-6exo), 2.20 (bd, 1H, H-4), 2.00 (m, 1H, H-6endo), 1.81 (bd, 1H, H-7b), 1.10–1.20 (m, 1H, H-5), and 0.65–0.71 (m, 1H, H-5b). $^{13}$C NMR ($d_6$-DMSO/CDCl$_3$) δ164.7 (s, C-3'), 140.7 (d, C$_5$'), 62.4 (d, C-3), 60.1 (t, C-2), 56.8 (t, C-7), 52.1 (t, C-6), 41.8 (d, C-4), and 26.7 (t, C-5). Analysis: theory: C, 53.61; H, 7.31; N, 39.08. found: C, 53.73; H, 7.35; N, 39.03.

Insecticidal Method

A broad variety of insect and arachnid species can be controlled by contact of a compound of Formula I and Formula II with the insect or its locus. Many insects and arachnids that are commercially important because they are detrimental to agriculture, to public health, and to buildings can be killed or controlled. Insects of the order homoptera, and especially those of the family cicadellidae, which are generally sucking insects, are particularly well controlled. Cotton aphids, aster leafhoppers, brown planthoppers (*Nilapatvata lugens*), and green leafhoppers (Nephotettix green leafhoppers (*Nephotettix cinciteps*) are examples of such insects. Insects of other orders, including lepidoptera, diptera, heteroptera, thysanoptera, are controlled as well. Arachnids of the order acarina, especially those of the family acaridae, which are generally phytophageous, sucking mites, are particularly well controlled. The two-spotted spider mites (*Tetranvchus urticae*) are an example of such arachnids. Insects and arachnids are killed or controlled to some extent at each stage of their life cycle. Their kill or control while in the adult stage (adulticidal activity) is particularly strong and their kill or control while in the egg stage (ovicidal activity) is also strong in many cases, especially with certain acarina species.

Effective kill or control of insects and arachnids is achieved by applying to the insects or arachnids or the locus thereof an insecticidal or acaracidal amount of a compound of Formula I or II or a compound that is converted to a compound of Formula I or II within the insects or arachnids. An amount that is effective varies depending on the specific compound employed, the composition in which the compound is applied, the method of application employed, the specific insects or arachnids, the life stage of the insects or arachnids, the location of the insects or arachnids, the climatic conditions of temperature, humidity, and wind speed, and other factors. Application rates as low as 1 g/Ha are sometimes effective under some circumstances and application rates as high as 1 Kg/Ha may be required under other circumstances. Generally, it is preferred to employ application rates of between about 5 g/Ha and about 500 g/Ha.

Control of Adult Two-spotted Spider Mites

A ten mg (milligram) sample of each test compound was dissolved in 0.5 mL (milliliter) of a formulation mixture composed of 88.75 percent acetone, 8.0 percent N-methyl-2-pyrrolidinone, 2.0 percent Exxon TM 200 hydrocarbon solvent and 1.25 percent Tween TM 20 surfactant and the resulting solution was diluted to 50 mL with deionized water to obtain a 200 ppm (parts per million) spray mixture. Mixtures of lower concentration were prepared by serial dilution using a mixture of 49.5 mL of deionized water and 0.5 percent of the formulation mixture for dilution so as to achieve 4:1 dilutions. Fully expanded squash cotyledons were infested with a mixed population of two-spotted spider mites (*Tetranvchus urticae*) by applying infested leaf material bearing 10–20 adults to the upper surface and, after 24 hr, removing the donor leaf. The infested cotyledon leaves were treated by spraying each surface to runoff with 0.5 mL of a spray solution using a hand sprayer equipped with a Teejet TM TN-2 nozzle. Four replicates of each treatment were applied. Eight untreated controls were prepared by applying blank diluted formulation mixture in the same way. The plants were allowed to dry and then were kept in a chamber maintained at 25.5° C. and 70–80 percent relative humidity with a 12 hr:12 hr light-:dark cycle. After 72 hr the number of live adult female mites were counted. The efficacy of each test compound was then determined by comparing the average number of live adult female mites on the treated leaves (each test compound and each application rate) with the average number on the control leaves and calculated as a percentage. Some of the results are given in the activity summary table.

Control of Aster Leafhoppers.

A weighed sample of each test compound was dissolved in a known amount of acetone and the resulting solution was serially diluted with acetone to obtain solutions of known concentration. Generally, solutions containing four different concentrations of each test compound were prepared. A 0.5 mL portion of each solution or of acetone alone (blank) was pipetted into a 20 mL borosilicate glass scintillation vial and the treated vials were rolled on a Swelab TM roller-mixer until the acetone had evaporated, as indicated by the appearance of a slight, transient iridescence on the inner vial surface. Adult aster leafhoppers (*Macrosteles severini*) were collected from a colony, were anesthetized with carbon dioxide, and groups of 5–7 were aspirated into each vial. Each vial was capped with a reservoir made from a polyethylene Caplug TM by removing the bottom. Parafilm-M TM was stretched across the bottom surface of each reservoir and the reservoirs were placed in the vials with the parafilm surface facing the interior. A 1.0 mL portion of a 10 percent (w/v) aqueous sucrose solution was placed in each vial. The vials were then placed in racks and held in a controlled environment chamber at 23° C. and 50 percent relative humidity with a 16 hr:8 hr light:dark cycle. The mortality of the insects was determined after 24 hr, and, if the mortality in the acetone blank checks remained below 30 percent, after 48 and 72 hr. Leafhoppers which were unable to move or to right themselves when disturbed were counted as dead. The number of dead was corrected using Abbott's formula. Some of the results are given in the activity summary table.

Control of Green Leafhopper and Brown Planthopper

A weighed sample of each test compound was dissolved in a known amount of acetone and then a known amount of water so as to obtain a solution containing 12.5 percent acetone and the resulting solution was serially diluted with water containing 12.5 percent acetone to obtain solutions of known concentration. Generally, solutions containing four different concentrations of each test compound were prepared. Rice seedlings were prepared by washing soil from the roots. Circles of metal screen were prepared and a slit was cut from the outer edge to the center. Four rice seedlings were slipped through the slit inn each screen and each screen was then placed on a glass cup of about the same diameter filled with water so that the roots of the rice plants extended into the water. A glass cylinder of essentially the same diameter as the glass cup was placed on top of the metal screen on each cup and the cup and cylinder were taped together. A 0.5 mL portion of a test solution or of a solvent blank was sprayed into each cylinder. Generally, 4 cylinders were treated with each test solution. Three hours after spraying 5 third-instar green leafhopper (*Nephotettix cinciteps*) or brown planthopper (*Nilaparvata lu~ens*) nymphs were taken from a colony by aspiration and transferred to each cylinder. Each cylinder was capped with a screened lid, placed in a rack, and held in a controlled environment chamber at 28° C. and 75 percent relative humidity with a 14 hr:10 hr light:dark cycle. The mortality of the insects was determined after 48 hr. The number of dead insects was corrected using Abbott's 30 formula, as described in Abbott, W. S. *J. Econ. Entomol.*, 1925, 18, 265–267.

| | PERCENT MORTALITY AT 50 PPM | | | |
|---|---|---|---|---|
| Compound | ALH | BPH | GLH | TSSM |
| 1 | 0 | NT | NT | 79 |
| 2 | 100 | NT | NT | 74 |
| 3 | 100 | 100 | 100 | 100 |
| 4 | 100 | 100 | 100 | 100 |
| 5 | 0 | NT | NT | 19 |
| 6 | 0 | NT | NT | 71 |
| 7 | 81 | 100 | 63 | 53 |
| 8 | 100 | 100 | 100 | 100 |
| 9 | 100 | 100 | 74 | 67 |

NT = Not Tested

Compositions

The compounds of the present invention can be used directly as insecticides and arachnicides, but it is generally preferable to first prepare a composition containing one or more of the compounds in combination with an agriculturally acceptable adjuvant or carrier. Suitable adjuvants or carriers should not be phytotoxic to valuable crops, should not be highly toxic to mammals, should be environmentally acceptable, and should not react chemically with compounds of Formula I or II or other composition ingredients. The insecticidal compositions can be designed for application directly to insects or arachnids or to their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions, or suspensions. Suitable agricultural adjuvants and carriers that are useful in preparing the insecticidal and acaricidal mixtures of the invention are well known to those skilled in the art.

Liquid carriers that can be employed include water, toluene, xylene, petroleum naphtha, crop oil, acetone, methyl ethyl ketone, cyclohexanone, trichloro-ethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application.

The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, Such as nonylphenol-clg ethoxylate; alcohol-alkylene oxide addition products, such as tridecyl alcohol-C16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternar amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The compositions can also contain other compatible components, for example, other insecticides and arachnicides, plant growth regulants, fungicides, herbicides, and the like and can be formulated with solid, particulate fertilizer carriers such as ammonium nitrate, urea and the like or with liquid fertilizers.

The concentration of the active ingredients of Formulas I and II in the insecticidal and arachnicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably from about 10 to about 90 weight percent. Such compositions are typically diluted with an inert carrier, such as water, before application. The diluted compositions usually applied to insects or arachnids or to their locus generally contain from about 0.001 to about 5 weight percent active ingredient and preferably contain from about 0.01 to about 1.0 percent.

The present compositions can be applied by the use of conventional ground or aerial dusters and sprayers, by addition to irrigation water, and by other conventional means known to those skilled in the art.

I claim:

1. A method of killing or controlling insects or arachnids which comprises contacting said insects or arachnids or the locus thereof with an insecticidal or arachnicidal amount of a compound of Formula I or Formula II:

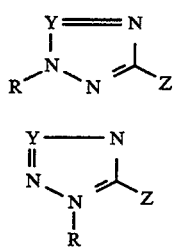

wherein
Y represents CH or N;
Z represents H, F, Cl, Br, CN, $CO_2R^1$, $CONH_2$, $CONHR^1$, $CONR^1R^1$, $OR^1$, $SR^1$, $NH_2$, $NHR^1$, $NR^1R^1$, $NHOR^1$, cyclopropyl, $CH=CH_2$, $C\equiv CR^2$, or $C_1$–$C_2$ alkyl optionally monosubstituted with F, OH, $OR^1$, $SR^1$, $NH_2$, $NHR^1$, $NR^1R^1$, $CO_2R^1$, $CONH_2$, $CONHR^1$, or $CONR^1R^1$;
$R^1$ is $C_1$–$C_2$ alkyl, $CH_2$—$C\equiv CH$, $CH_2$—$CH=CH_2$, benzyl, or cyclopropylmethyl;
$R^2$ is H or $SIR^3$;
$R^3$ is $C_1$–$C_4$ alkyl;
R is an aliphatic nitrogen containing heterocyclic moiety selected from groups $R_a$ through $R_k$ where $R_a$ through $R_k$ are as follows:

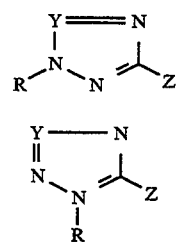

wherein
$R^4$ represents H or $C_1$–$C_2$ alkyl;
$R^5$ represents F, Cl, Br, OH, $CO_2R^1$, $C_1$–$C_4$ alkyl, or $C_1$–$C_4$ alkoxy;
n represents the integer 0, 1, or 2; or an agriculturally acceptable acid addition salt thereof; or otherwise causing an insecticidal or arachnicidal amount of said compound to be present within said insects or arachnids.

2. A method according to claim 1 wherein the compound is of Formula I wherein Y represents N.

3. A method of claim 1 wherein Z ms amino or methyl.

4. A method of claim 1 wherein R represents 1-azabicyclo[2,2,1]heptan-3-yl, or 1-azabicyclo [2,2,2]octan-3-yl.

5. A method according to claim 2 wherein R represents 1-azabicyclo[2,2,1]-heptan-3-yl and Z represents amino or methyl.

6. A method according to claim 1 wherein the insects are of the order homoptera.

7. A method according to claim 6 wherein the insects are brown planthoppers.

8. A method according to claim 1 wherein the arachnids are of the order acarina.

9. A method according to claim 8 wherein the arachnids are two-spotted spider mites.

10. A method according to claim 1 wherein the compound is applied to a valuable plant crop.

11. A method according to claim 10 wherein the crop is rice.

* * * * *